US012369808B2

(12) United States Patent
Kyriacou et al.

(10) Patent No.: US 12,369,808 B2
(45) Date of Patent: Jul. 29, 2025

(54) DEVICE AND METHOD FOR NON-INVASIVE PREDICTION OF INTRACRANIAL PRESSURE BASED ON OPTICAL MEANS

(71) Applicant: City, University of London, London (GB)

(72) Inventors: Panayiotis Kyriacou, London (GB); Tomas Abay, London (GB); Justin Phillips, London (GB); Christopher Uff, London (GB)

(73) Assignee: City, Universsity of London, London (GB)

( * ) Notice: Subject to any disclaimer, the term of this patent is extended or adjusted under 35 U.S.C. 154(b) by 374 days.

(21) Appl. No.: 17/777,644

(22) PCT Filed: Nov. 18, 2020

(86) PCT No.: PCT/EP2020/082598
§ 371 (c)(1),
(2) Date: May 18, 2022

(87) PCT Pub. No.: WO2021/099426
PCT Pub. Date: May 27, 2021

(65) Prior Publication Data
US 2022/0409080 A1 Dec. 29, 2022

(51) Int. Cl.
*A61B 5/03* (2006.01)
*A61B 5/00* (2006.01)
(52) U.S. Cl.
CPC ............ *A61B 5/031* (2013.01); *A61B 5/0075* (2013.01); *A61B 5/6814* (2013.01);
(Continued)
(58) Field of Classification Search
CPC .......... A61B 5/0075; A61B 2562/0238; A61B 2562/0242; A61B 2562/043;
(Continued)

(56) References Cited

U.S. PATENT DOCUMENTS

2009/0234245 A1   9/2009   Jaffe et al.
2011/0201961 A1   8/2011   Hu et al.
(Continued)

OTHER PUBLICATIONS

Davide Tamborini et al: Development and characterization of a multidistance and multiwavelength diffuse correlation spectroscopy system:, Neurophotonics, vol. 5, No. 01, Sep. 21, 2017 (Sep. 21, 2017). p. 1 See International Search.
Farzam Parisa et al: "Fast diffuse correlation spectroscopy (DCS) for non-invasive measurement of intracranial pressure (ICP) (Conference Presentation)", Progress in Biomedical Optics and Imaging, SPIE—International Society for Optical Engineering, Bellingham, WA, US, vol. 10050. Feb. 8, 2017 (Feb. 8, 2017), pp. 100500U-100500U See International Search.
(Continued)

*Primary Examiner* — Amelie R Davis
(74) *Attorney, Agent, or Firm* — Finch & Maloney PLLC

(57) ABSTRACT

A system for in-vivo monitoring of intracranial pressure is provided. The system includes a probe and a controller. The probe includes optical emitters and optical detectors. The optical detectors detect light emitted by the optical emitters generate signals representative of the detected light. The controller includes memory and processor. The controller connects to the probe to energize the optical emitters and receiving signals from the optical detectors. The system may include modelling, extraction, and pressure prediction modules. The modelling module can relate intracranial pressure to features of an optical signal representative of a degree to which light input into a subject's skull is absorbed by the subject's brain. The extraction module can extract signal features from a signal derived from the optical signals output by the detectors. The pressure prediction module can input the signal features into the modelling module and output an indication of intracranial pressure.

11 Claims, 8 Drawing Sheets

(52) U.S. Cl.
CPC .......... *A61B 5/7275* (2013.01); *A61B 5/7278* (2013.01); *A61B 5/7267* (2013.01); *A61B 2562/0238* (2013.01); *A61B 2562/0242* (2013.01); *A61B 2562/043* (2013.01)

(58) Field of Classification Search
CPC ..... A61B 5/0261; A61B 5/031; A61B 5/6814; A61B 5/7264; A61B 5/7267; A61B 5/7275; A61B 5/7278; A61B 5/03
See application file for complete search history.

(56) References Cited

U.S. PATENT DOCUMENTS

| 2016/0058395 A1 | 3/2016 | Muser et al. |
| 2016/0192849 A1 | 7/2016 | Galea |
| 2018/0103861 A1 | 4/2018 | Sutin et al. |
| 2019/0261869 A1* | 8/2019 | Franceschini ........ A61B 5/7203 |

OTHER PUBLICATIONS

Alexander Ruesch et al: "Intracranial Pressure Changes Derived from Near Infrared Spectroscopy Measurements in Non-Human Primates", Biophotonics Congress: Biomedical Optics Congress 2018 (Microscopy/Translational/Brain/OTS), Jan. 1, 2018 (Jan. 1, 2018), p. OW4C.3 See International Search.

Alexander Ruesch et al: Diffuse correlation spectroscopy for intracranial pressure estimation through cardiac pulse waveform analysis:, Diffuse Optical Spectroscopy and Imaging VII, vol. 11074. Jul. 11, 2019 (Jul. 11, 2019), p. 20 See International Search.

International Search Report Corresponding to PCT/EP2020/082598 mailed Feb. 8, 2021.

Written Opinion Corresponding to PCT/EP2020/082598 mailed Feb. 8, 2021.

* cited by examiner

DEVICE AND METHOD FOR NON-INVASIVE PREDICTION OF INTRACRANIAL PRESSURE BASED ON OPTICAL MEANS

CROSS-REFERENCE TO RELATED APPLICATIONS

This application claims priority under 35 U.S.C. § 371 as a national stage application of PCT Application No. PCT/EP2020/082598, filed Nov. 18, 2020, which claims priority to GB 1916782.4, filed Nov. 18, 2019, each of which is hereby incorporated herein by reference in its entirety.

FIELD

This disclosure relates to monitoring systems, particularly but not exclusively to systems for monitoring intracranial pressure and other physiological parameters. In one illustrative implementation, the system is operable to continuously and non-invasively monitor intracranial pressure.

In one illustrative application, the system of a preferred embodiment is particularly useful in the context of patients presenting with head injuries, and in the following detailed description particular emphasis will be placed on this particular application of the teachings disclosed herein. It is important to remember, however, that this application is merely illustrative, and that the system embodying the teachings disclosed herein could also facilitate research and clinical monitoring in non-head injury medicine, such as liver failure, migraine, diabetes, anaesthesia, intensive care, renal medicine etc.

BACKGROUND

Head injuries are a significant cause of injury and death, with approximately 50,000 cases of severe traumatic brain injury per year in the UK, the majority leading to death or severe disability. Cerebral damage sustained at the time of impact is referred to as primary injury and is irreversible and best treated by prevention (seatbelts, cycle helmets etc). Secondary brain injury occurs after the initial injury and is defined as damage arising from the body's physiological response to the primary injury. This may be as a result of bleeding or swelling of brain tissue.

As the skull is a closed cavity containing water and other largely incompressible material, even minor swelling can cause significant increase in intracranial pressure (ICP).

Initially, cerebrospinal fluid and venous blood are displaced (as described in the Munro-Kellie doctrine) but once these reservoirs are exhausted, small increases in pressure are transmitted directly to the brain tissue, compromising the arterial blood supply and reducing oxygen and glucose delivery to the brain tissue. This in turn results in further brain swelling which further compromises blood supply. Severe hypoxic brain injury can result, leading to irreversible brain damage.

Various strategies exist to arrest or reverse this process and in that connection, monitoring ICP is a vital tool in the management of severe head injuries. The "gold standard" technique for ICP monitoring is a catheter inserted into the frontal horn lateral ventricle via a right frontal burr hole, connected to a pressure transducer via a fluid-filled catheter. This arrangement has the advantage of allowing therapeutic drainage of cerebrospinal fluid (CSF) and administration of drugs. It is the case, however, that insertion may be difficult if the ventricles are small, and even if performed in a sterile environment infection occurs in approximately 11% of patients. Ventricular catheters measure global ICP and have the additional advantages of allowing periodic external calibration. Most clinicians now use electrical or fibre optic pressure transducers that are inserted into the brain tissue in the right frontal lobe via a twist drill hole (which is smaller than a burr hole). Although these are easier to insert and carry a lower infection risk, they are prone to drift and despite being less invasive than a ventricular catheter, they still carry a small risk of causing significant intracranial bleeding.

Whilst there has been much research in recent years to find a method for measuring intracranial pressure noninvasively (nICP) (including measurement of pressure in the retinal veins, measurement of eardrum displacement, transcranial Doppler ultrasonography and imaging-based solutions), it is the case that none of these methods have found their way into clinical use as they all require considerable user intervention and are non-continuous.

A recent review in Nature Reviews: Neuroscience reported that ICP monitoring is still a standard of care for traumatic brain injury patients and that there has been much recent interest in the potential of new non-invasive ICP monitoring techniques. Methods using tympanic membrane displacement and ultrasound "time of flight" techniques have been described, and whilst both are a poor surrogate for invasive ICP measurements, serial intra-patient measurements may be useful to determine temporal changes in ICP.

More recently, transcranial Doppler ultrasonography has been used to provide an indirect estimation of cerebral perfusion pressure ((CPP) i.e. the difference between mean arterial blood pressure and ICP) to an accuracy of ±10-15 mmHg, however these systems are expensive and as they require user intervention, they do not provide continuous monitoring and can only be used in a high dependency hospital environment.

It is estimated that in the UK, approximately 1 million patients attend hospital with a head injury per year, or which 5% are classed as severe. Of those with severe TBI, over 85% remain disabled after one year and 15% have not returned to work after five years. Traumatic injury kills more people below the age of 45, than any other cause, accounting for 18,000 deaths per year in the UK. Road traffic accidents are the most common cause of head injuries and are especially common in teenagers and young adults.

The care received by the patient (in the 'golden hour') immediately after injury may profoundly affect the outcome. This has resulted in the inception of pre-hospital medicine where care is directed towards ABC (securing the airway, oxygenating the patient and maintaining circulation), however little thought is given to head injury until the patient arrives in hospital. Even after arrival in a specialist hospital it may be up to an hour before definitive imaging is performed and surgery or ICP directed therapy is instituted. This paradigm is changing and pre-hospital SOPs (Standard Operating Procedures) now administer drugs to reduce ICP if there is evidence of a head injury, but this is a blind treatment. Pre hospital or immediate in-hospital ICP monitoring would allow ICP directed therapy from the outset.

There is significant evidence to suggest that therapy directed to maintain brain tissue oxygenation as well as ICP/CPP is associated with reduced mortality after severe TBI. Multimodality intracranial monitoring is now widely used during neurointensive care to provide early warning of impending brain ischemia and guide targeted therapy to improve cerebral perfusion and oxygenation.

Despite its limitations, ICP monitoring remains central to the monitoring and management of severe TBI. Conventional approaches to management have concentrated on a reduction in ICP to prevent secondary cerebral ischemia. Treatment is usually initiated if ICP increases >20 mm Hg, although it is likely that the duration of intracranial hypertension and its response to treatment are also important prognostic indicators.

Advances in MRI functional imaging have brought a revolution in our understanding of the brain. In particular, the mechanism of spinal cord and brain injury is much better understood, however this knowledge has not yet led to significant improvements in injury management, partly due to lack of clinical monitoring data at the bedside. Intensive care and emergency medicine are also in a state of flux with increased emphasis on goal directed therapy and realisation of the importance of early intervention to recovery and survival rates.

Aspects of the arrangements disclosed herein have been devised with the foregoing problems in mind.

SUMMARY

In accordance with a presently preferred arrangement, there is provided a system for non-invasive in-vivo monitoring of intracranial pressure, the system comprising: a probe comprising a plurality of optical emitters and a plurality of optical detectors; the optical detectors being configured to detect light emitted by the optical emitters and to generate signals representative of said detected light; and a controller comprising memory and a processor, the controller being connectable to the probe for energising the optical emitters and receiving signals from the detectors; the system further comprising a modelling module for establishing a model relating features of an optical signal to intracranial pressure, the optical signal being representative of a degree to which light input into a subject's skull is absorbed by the subject's brain; a feature extraction module operable to extract one or more signal features from an absorbance signal derived from the optical signals output by said detectors; and an intracranial pressure prediction module operable to input said signal features into said model and output an indication of intracranial pressure in accordance with said model.

In another implementation, there is provided a monitoring system comprising: a plurality of optical sources; a plurality of detectors, means operable to switch the optical sources on and off, means for receiving signals from the detectors; means operable to generate from said received signals a signal representative of light absorption by brain tissue (for example); and means operable to determine a measure of intracranial pressure from said brain tissue absorbance signal.

Other aspects of the teachings disclosed relate to a probe for such systems, and a controller for such systems. Various preferred features of arrangements disclosed herein are set out in the accompanying claims.

BRIEF DESCRIPTION OF THE DRAWINGS

Various aspects of the teachings disclosed herein, and arrangements embodying those teachings, will hereafter be described by way of illustrative example with reference to the accompanying drawings, in which.

DETAILED DESCRIPTION

Figure 1:
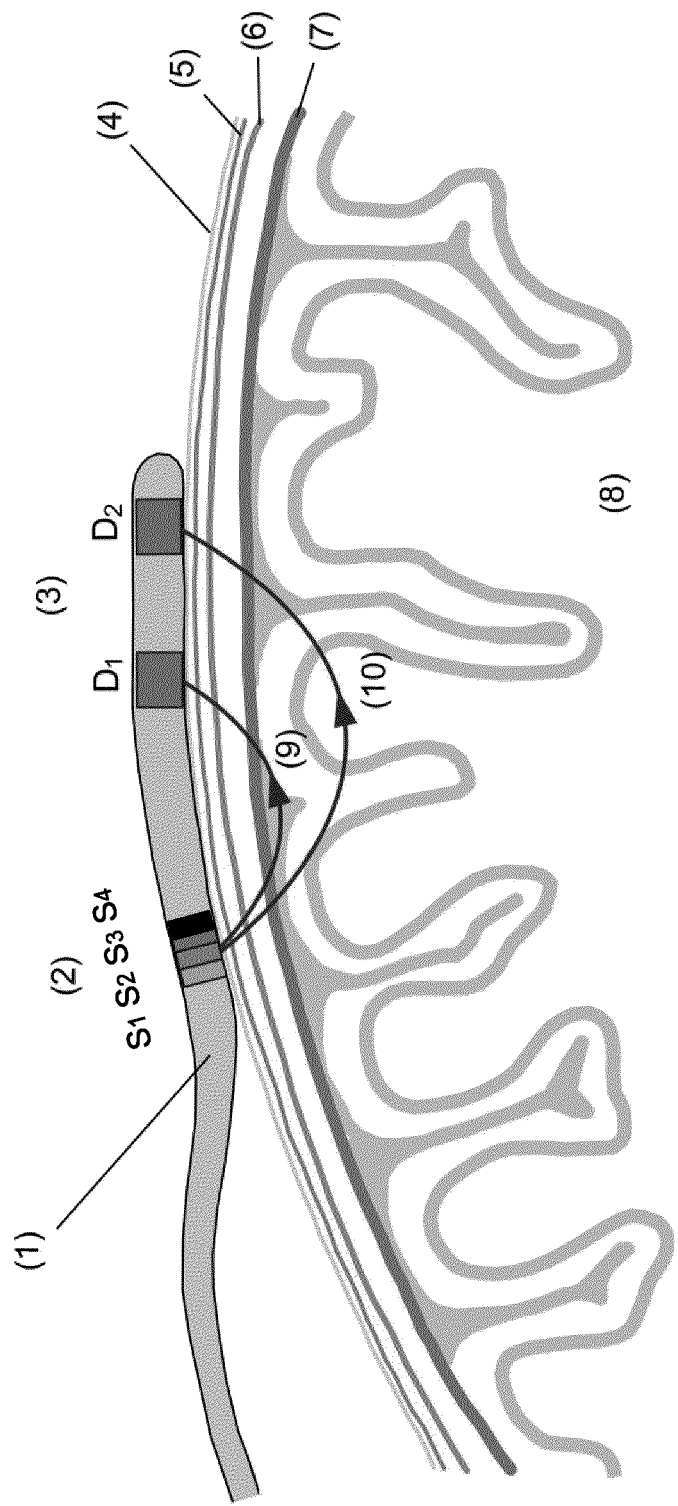
FIG. 1 is a schematic representation of a non-invasive probe for a monitoring system embodying the teachings of the present invention.

Referring now to FIG. 1, there is depicted a schematic representation of a non-invasive probe (1) for use with a monitoring system embodying the teachings of the present disclosure.

The probe (1) contains multiple near-infrared/infrared sources (2), each capable of emitting light of a different wavelength or band of wavelengths. The sources can be switched on and off as needed. A pair (or more) of detectors (3) is also contained within the probe. The detectors are spaced from one another within the probe—for example by a few millimetres to one or more centimetres.

In a preferred implementation, the sensor contains an array of four optical sources that are capable of emitted light of different wavelengths. In this arrangement the sources comprise light emitting diodes emitting light of four different wavelengths in the near infrared/infrared. The two detectors (3) comprise photodetectors (for example, photodiodes) located at different distances from the sources. In one implementation the first detector D1 is 1 cm from the sources and the second detector D2 is 3.5 cm from the sources. In this particular example, the sources are operable to emit light of 810 nm, known as the principal wavelength, and three other secondary wavelengths 770 nm, 855 nm and 880 nm. Light having a wavelength in the range between 805-810 nm is at the isobestic point, where oxygenated and deoxygenated haemoglobin have the same optical absorption properties. As such, this principal wavelength provides signals that are independent from the oxygenation of blood. In other implementations light of 780, 805, 850 and 870 nm may be emitted in place of or in addition to any of the aforementioned wavelengths.

The probe (1) is secured to the forehead epidermis (4) of a patient, and the infra-red sources are operable to illuminate the dermis (5), skull (6), dura mater (7), and the frontal lobe of the brain (8) (part of cerebral cortex). Reference numerals (9) and (10) indicate, respectively, the mean optical path between a given source and a proximal detector (D1) of said pair of detectors (3); and the mean optical path between a given source and a distal detector (D2) of said pair of detectors. In a preferred arrangement multiplexing and demultiplexing the sources and detectors results in eight acquired signals (2 detectors×4 wavelengths) which are reduced to four signals representing the absorbance of brain tissue at each of the aforementioned wavelengths.

Light from one of the sources (e.g. S2) penetrates the tissue and is detected by both detectors. The proximal detector (D1) detects light from the superficial (extra-cerebral) layers (4-7), while the distal detector (D2) detects light from the superficial and deeper brain (cerebral) layers (4-8).

The probe is coupled to a controller (not shown) that is configured to send signals to the probe (1) to activate and deactivate the sources (2), and to receive signals from the detectors (3). The controller is operable to process signals received from the detectors, in particular to calculate the degree to which light input into the skull of the patient is absorbed by the superficial and deeper brain layers.

Figure 2A:
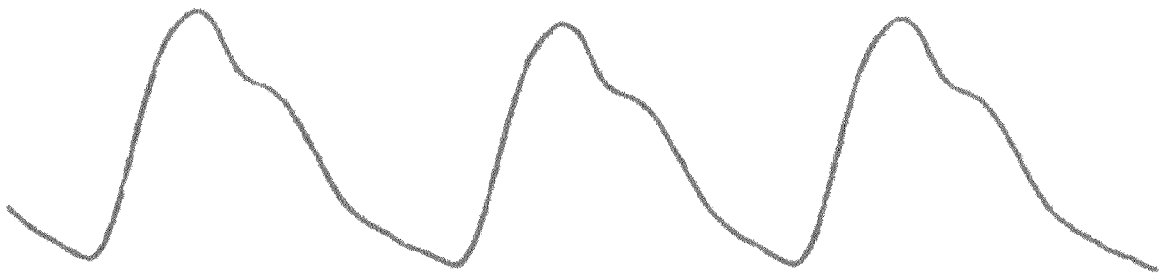
FIG. 2(a) is an illustrative representation of absorbance calculated from the signals detected at the first detector D1.
Figure 2B:
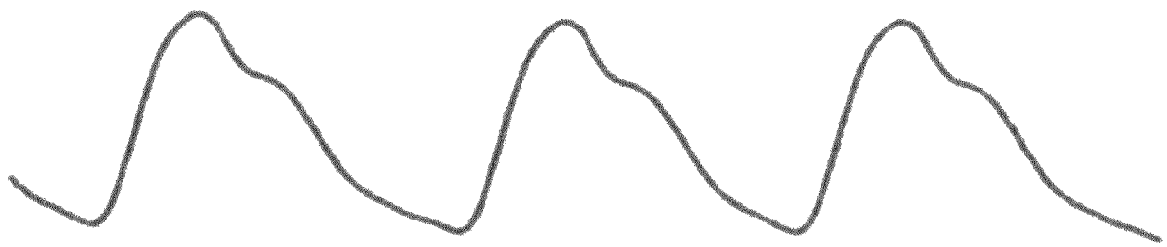
FIG. 2(b) is an illustrative representation of differential absorbance calculated by subtracting the D1 detector signal from the D2 detector signal.

Absorbance of light is calculated from the light intensity detected by D1 and D2 using the Beer-Lambert Law (A=In (Io/I) where Io and I are incident and detected intensity respectively). Subtracting the absorbance signal from D1 from the absorbance from D2 gives absorbance signal for deep brain tissue only (since this represents the difference in optical path through the tissue). Thus the effects of extra-cerebral tissue from the optical path is reduced (ideally, substantially eliminated). Alternatively, signal processing techniques such as independent component analysis or blind signal separation can be used to subtract absorbance D1 from the absorbance of D2, using the absorbance at D1 as reference signal. FIG. 2(a) is an illustrative representation of the absorbance calculated from the signals detected at the first detector D1, and FIG. 2(b) is an illustrative representation of the differential absorbance calculated by subtracting the D1 detector signal from the D2 detector signal. The depth of penetration of the light may be controlled by selecting appropriate wavelengths of light (by switching on a particular source) because longer wavelengths of near-infrared light penetrate tissue more deeply than short wavelengths. Alternatively, a larger emitter-detector separation distance >3.5 cm can be used to increase penetration. As will be appreciated, light detected by the detectors will be modulated by pulsation of the cerebral arteries. Changes in the pressure surrounding the cerebral arteries will thus affect the morphology and other characteristics of the recorded optical pulse, and the controller is configured to analyse certain quantifiable features of the acquired signal and thus generate a measure of non-invasive ICP (nICP).

In an envisaged arrangement, the controller is coupled to a display for displaying a generated measure of nICP to clinicians, and may be configured to provide warnings (for example, a visual and or sonic warning) in the event that nICP changes, for example exceeds a predetermined threshold.

In an envisaged implementation, the controller may comprise a portable processor, for example a so-called laptop computer. Alternatively, the controller may be configured as a dedicated portable device. Such an implementation would provide a particularly useful tool for paramedics or doctors working on a patient outside of a hospital. In another envisaged implementation, the controller may be incorporated into other types of monitoring apparatus for use inside of a hospital. As will be appreciated by persons of ordinary skill in the art, the functionality provided by the controller may be implemented—at least partly—by one or more software modules.

Inside the cranial cavity the brain is surrounded by cerebrospinal fluid. The cerebral vasculature includes arterioles, venules and capillaries. Since the cranial cavity is rigid, the total volume is constant. Arterioles are thick walled vessels containing layers of smooth muscle, containing blood at variable pressure. Changes in arteriolar volume due to the pulse create inverse changes in the venule and capillary volumes (since brain tissue and cerebrospinal fluid are incompressible). Arterial pulsation is detectable using light in the ~900 nm region. The pulsation of venules and capillaries show inverse pulsation, detectable using 750 nm light.

Figure 3:
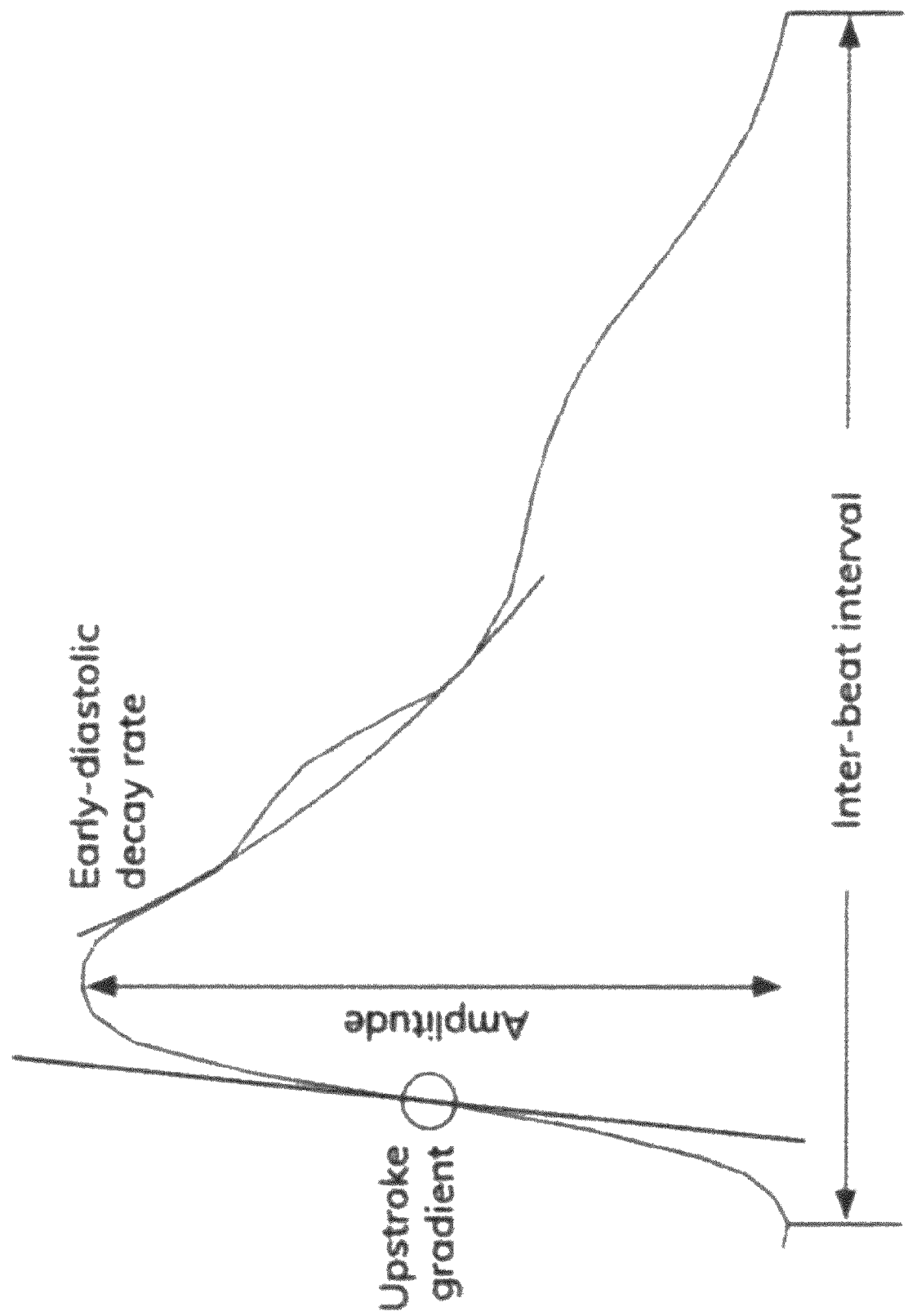
FIGS. 3 and 4 are diagrammatic representations of illustrative features of an absorbance signal.
Figure 4:
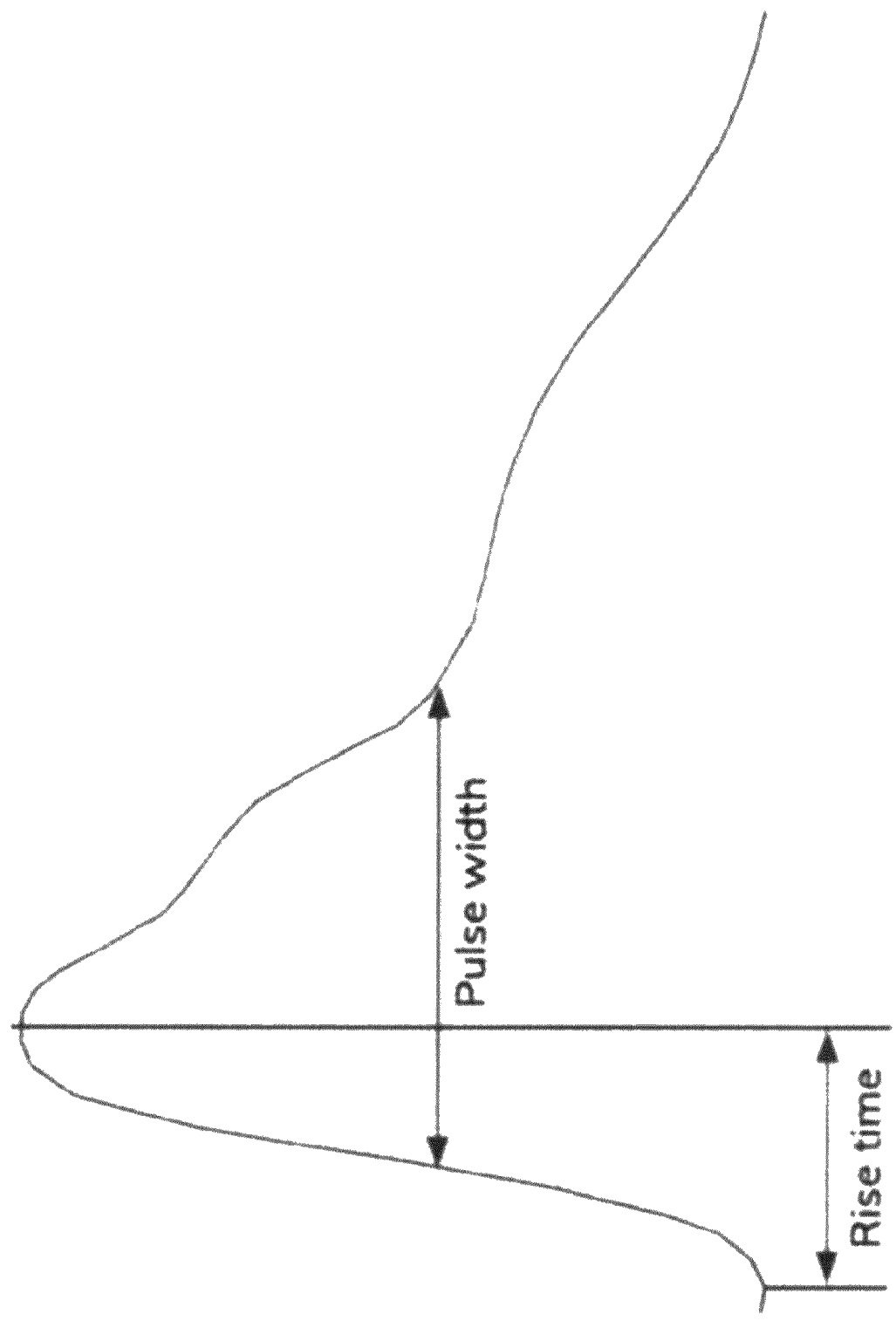

Several features are extracted from each pulse waveform and averaged over a rolling-window of, in this particular implementation, approximately 15 seconds. These features are shown in FIGS. 2 and 3 of the accompanying drawings, and there follows below a brief explanation of their relation to intracranial pressure values. Note that all the features discussed below are applicable to the 805-810 nm waveform (i.e. the signal obtained at the principal-isobestic wavelength) unless otherwise stated.

Pulse Amplitude

The pulse amplitude (i.e. the height of the wave from foot to peak), normalised dividing by total light intensity is positively correlated with ICP. This is because the intracranial pressure facilitates emptying of the arterioles during diastole (effectively lowering the 'foot' of the wave). We have determined, except at very high ICP values, that the amplitude pulse amplitude varies approximately linearly with ICP.

Upstroke Gradient

Upstroke (or upslope) gradient is positively correlated with ICP, since the arterioles are emptier at the beginning of systole when ICP is elevated compared with normal values.

Rise Time

The rise time is normalised dividing by the inter-beat interval. We have determined that the rise time (time taken to reach peak amplitude) is positively correlated with ICP for the reason stated for the upstroke gradient above, i.e. end-diastolic emptying of arterioles requires longer filling time during systole. Note that increased ICP causes the peak of the waveform to arrive slightly earlier (since expansion of the vessel ceases when internal and external pressures become equal), which may decrease correlation of rise time with ICP to some extent.

Early Diastolic Decay Rate (EDDR)

The decay rate can be found by fitting an exponential function to the diastolic runoff (downstroke) of the waveform and is normalised dividing by the peak amplitude. We have determined that the decay rate value is positively correlated with ICP because elevated ICP facilitates faster emptying of the arterioles.

Pulse Width (Negative Correlation with ICP)

The pulse width, measured at the mid-point between the foot and peak of the wave on the y-axis, is negatively correlated with ICP for the reason stated for EDDR, i.e. because elevated ICP facilitates faster emptying of the arterioles.

Late Diastolic Area Under Curve

Figure 5:
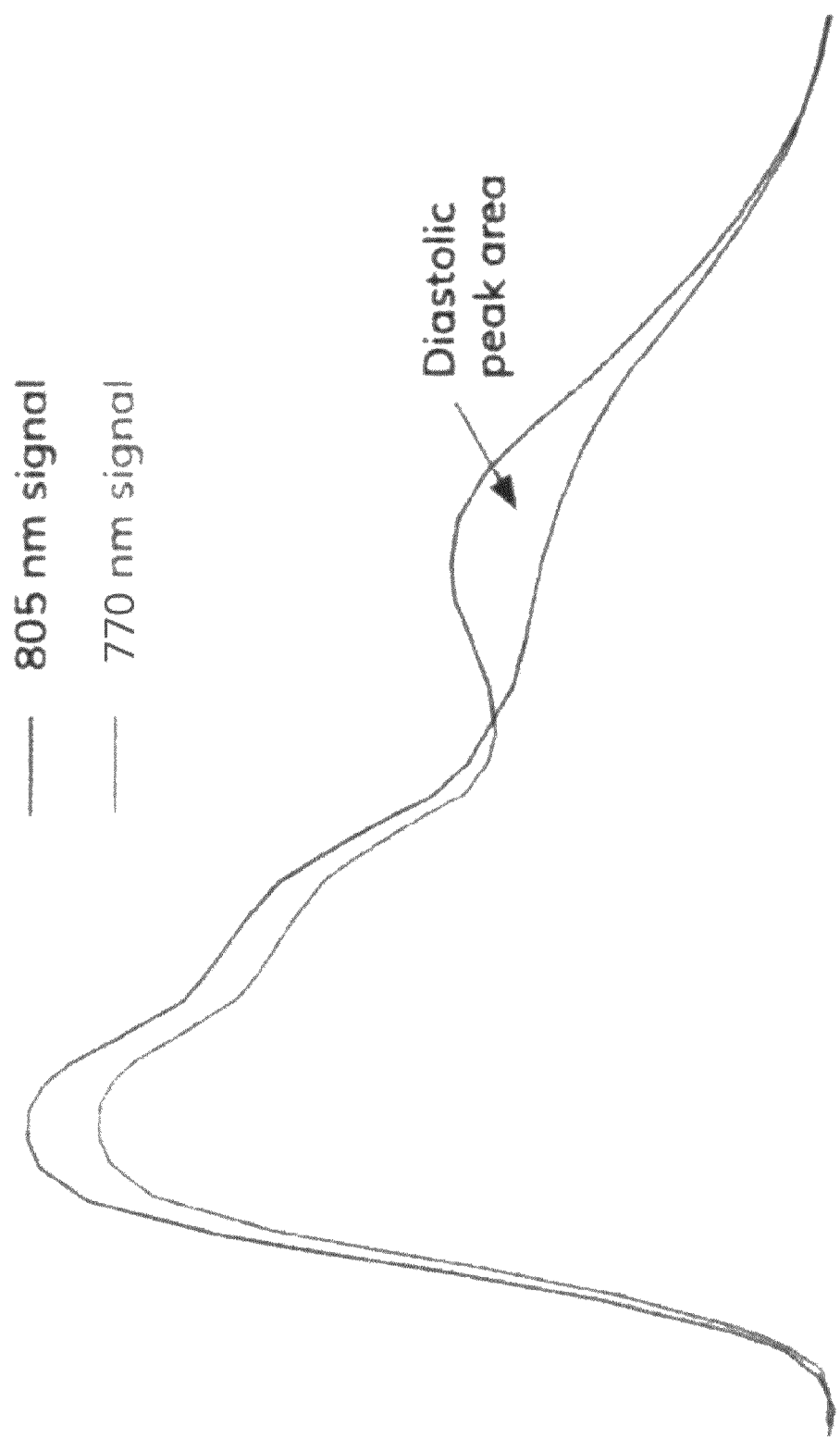
FIG. 5 is a diagrammatic representation of diastolic peak area.

A secondary peak appearing in the later part of the waveform relates to filling of the venules from capillary blood as well as back-filling from larger veins when supine (cerebral veins do not contain valves to prevent this unlike most systemic veins). The process is impeded by elevated ICP, since the ICP exerts pressure on the exterior wall of the vessels preventing them from filling. The area under the later part of the curve, normalised by dividing by the total area under the pulse is indicative of the volume of the pulse. Comparison of the waveforms obtained at the principal wavelength and a shorter wavelength (see FIG. 5) provides an estimation of the area of the secondary peak since venous blood contains significant deoxyhaemoglobin, which absorbs shorter wavelength near infrared light more strongly than longer wavelengths.

Note that filling of the arterioles during systole causes emptying of the venules (as well as capillaries), effectively causing pulsation of the venules. This has been observed in the brain as well as in non-cerebral tissue.

Total Backscattered Intensity

The total backscattered intensity is indicative of blood volume. Elevated ICP effectively 'squeezes' blood from the brain, leading to less absorption of light passing through the brain tissue and higher detected intensity. The intensity is therefore positively correlated with ICP. This quantity should be averaged over the length of the sampling window (for example, c. 15 s).

Decay Time

Figure 6A:
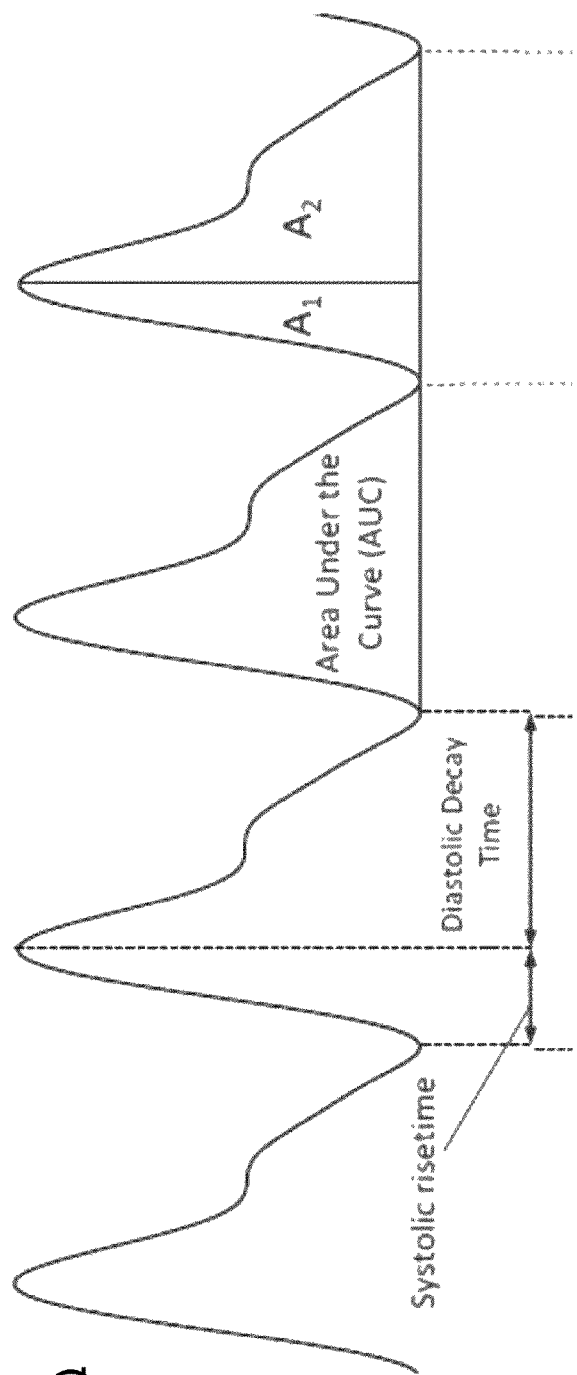
FIG. 6(a) is a diagrammatic representation of other features of the absorbance signal.

As shown in FIG. 6(a), the time from the pulse's peak to the pulse's valley. Also defined as the time (duration) of the diastolic period of the pulse.

Area Under the Curve (AUC)

The area under the entire pulse's profile or waveform (see FIG. 6(a)).

AUC Ratio

The AUC ratio is defined as the ratio between the area under the curve of the systolic period of the pulse (A1) and the area under the curve of the diastolic period (A2). (AUC Ratio=A2/A1), and is used as an indicator of vascular resistance, which varies with intracranial pressure.

Second Derivative Pulse Ratio

Figure 6B:
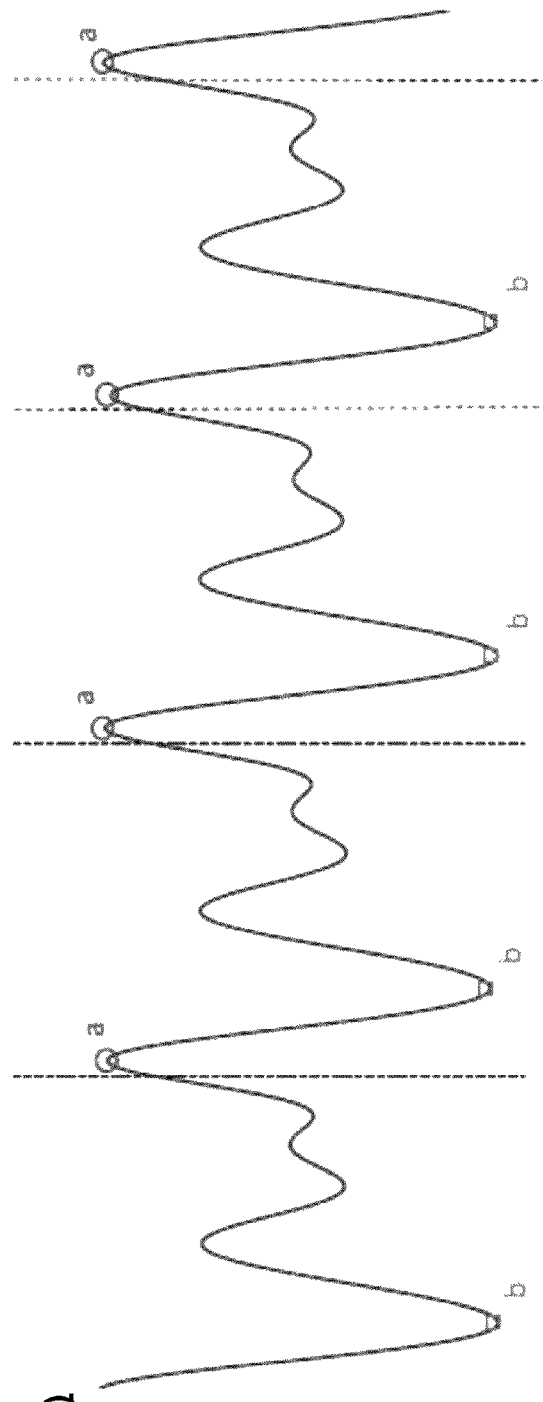
FIG. 6(b) is a diagrammatic representation of a first derivative of the signal shown in FIG. 6(a)

With reference to FIG. 6(b), the second derivative pulse ratio is defined as the ratio of the point b and point a of the first derivative of the pulse signal and is representative of an indicator of arterial stiffness, which tends to vary with intracranial pressure.

Figure 6C:
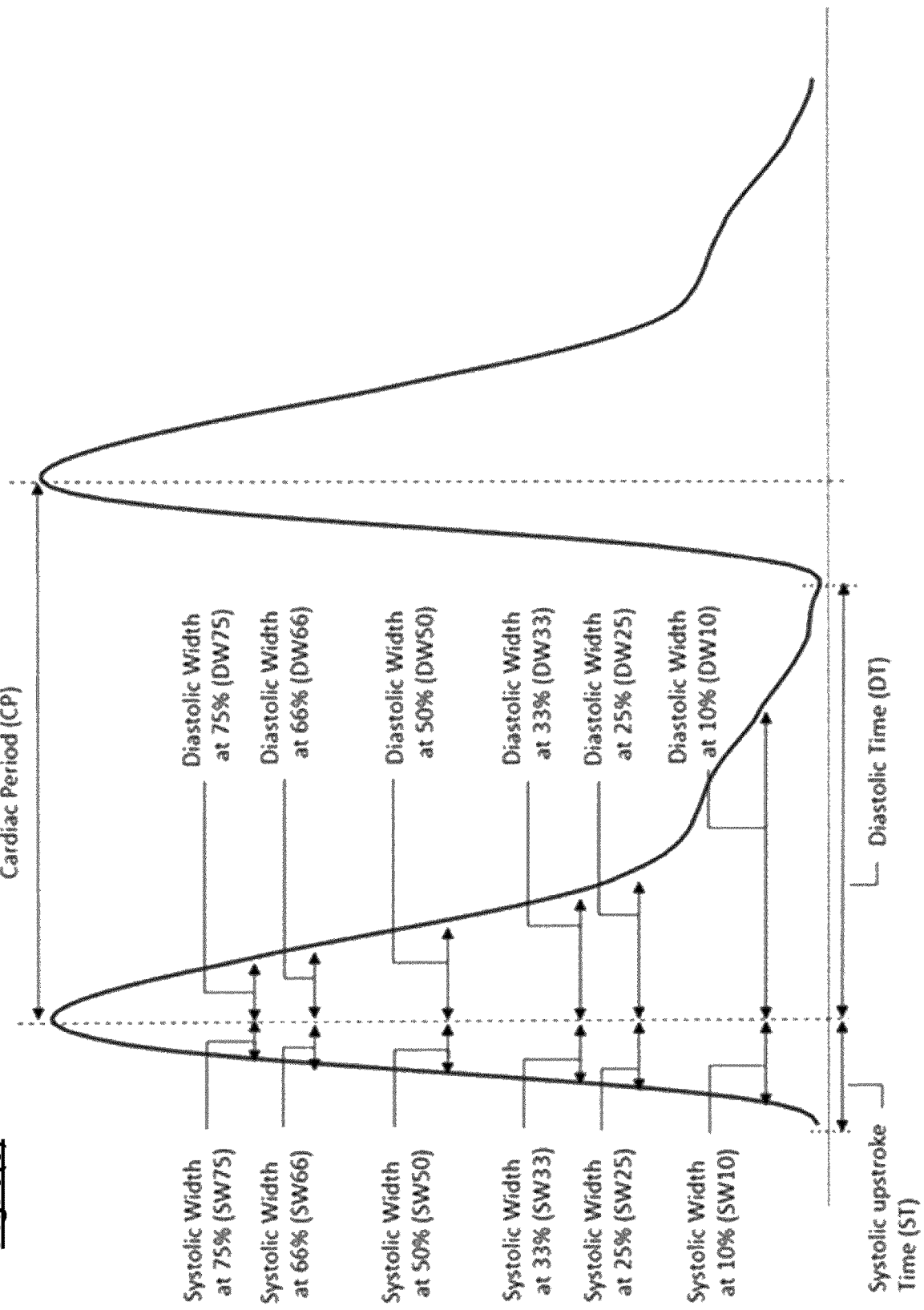
FIG. 6(c) is a diagrammatic representation of other features of the absorbance signal.

Other features of interest, some of which are shown in FIG. 6(c), are set out in the table below.

TABLE 1

Illustrative features extractable from pulse waveform

| Feature | Calculation |
|---|---|
| PPG raw | |
| Systolic amplitude - X | systolic peak |
| Diastolic amplitude - Y | diastolic peak |
| Dicrotic notch - Z | dicrotic peak |
| pulse widths @: | |
| at 10% | DW10; DW10 + SW10; DW10/SW10 |
| at 25% | DW25; DW25 + SW25; DW25/SW25 |
| at 33% | DW33; DW33 + SW33; DW33/SW33 |
| at 50% | DW50; DW50 + SW50; DW50/SW50 |
| at 66% | DW66; DW66 + SW66; DW66/SW66 |
| at 75% | DW75; DW75 + SW75; DW75/SW75 |
| systolic area A1 | systolic area |
| diastolic area A2 | diastolic area |
| Pulse area or inflection point ratio (A2/A1) | diastolic area/systolic area |
| peak to peak interval | time difference between 2 consecutive peaks |
| Pulse interval time (PI) | pulse time from foot to end of waveform |
| ratio PI/X | PI/X |
| Heart rate | 60/PI |
| Augmentation Index | Y/X |
| Large Artery Stiffness Index | $(h/\Delta T)$ |
| Crest time or systolic upstroke time (ST) | time from foot to the peak |
| Diastolic time (DT) | time from peak to end of cycle |
| ratio of ST over PI time | ST/PI |
| ratio of DT over PI time | DT/PI |
| Dicrotic notch time | |
| $\Delta T$ | time diff between x and y |
| main wave rising slope (max_s) | values of the PPG at first deriv peak index |
| Relative height of max slope point | Height_max_s/X |
| time between the max slope index and peak (T_max_slope) | time between max slope index and peak index |
| ratio of T_max_slope over PI | T_max_slope/PI |
| diastolic peak falling slope | y/(PI- dicrotic peak time) |
| PPG Intesity Ratio (PIR) | Ratio of PPG peak intensity to PPG bottom intensity (X/ppg_foot) |
| PPG_K value | k = (PPG_m − PPG_foot)/(PPG_peak − PPG_foot) where PPG_m = (1/PI) ∫ PPG(t)dt |
| First derivative | |
| $\Delta T$ | time diff between the two positive to negative zero crossing. Or between PPG peak and local max |
| peak amplitude (a1) | peak height |
| first peak time (t_a1) | time from foot to peak |
| valley time (t_b1) | time from peak to local minima (first valley) |
| ratio peak time to PI | t_a1/PI |
| ratio t_b1 to PI | t_b1/PI |
| second peak time (t_e1) | time from foot to second local maxima (occurs after the first valley) |

TABLE 1-continued

Illustrative features extractable from pulse waveform

| Feature | Calculation |
|---|---|
| Second derivative | |
| a value- peak | peak intensity -height |
| b- foot height | foot intensity |
| ratio A__b/A__a | A__b/A__a |
| ratio AP__b/AP__a | amplitude of AP__b over AP__a |
| ratio A__c/A__a | |
| ratio A__d/A__a | |
| ratio A__e/A__a | amplitude of A__e over A__a |
| AP__e/AP__a | amplitude of AP__e over AP__a |
| peak time t__a2 | time from foot to peak |
| time interval between a and b (t__b2) | time from peak to local minima |
| time interval between b and e (t__c2) | time from local minima to peak point e |
| total intensity | height between peak and local minima |
| ratio peak time to PPG PI | t__a2/PI |
| ratio t__b2 to PI | t__b2/PI |
| ratio t__c2 to PI | t__c2/PI |

The intracranial pressure can be calculated, for example by the aforementioned controller, using a simple algorithm based on a small number of features, selected from those that show the best correlation with ICP. A simple linear or nth-order function, calibrated from clinical trial data, may be used to convert features into ICP values.

Figure 7:
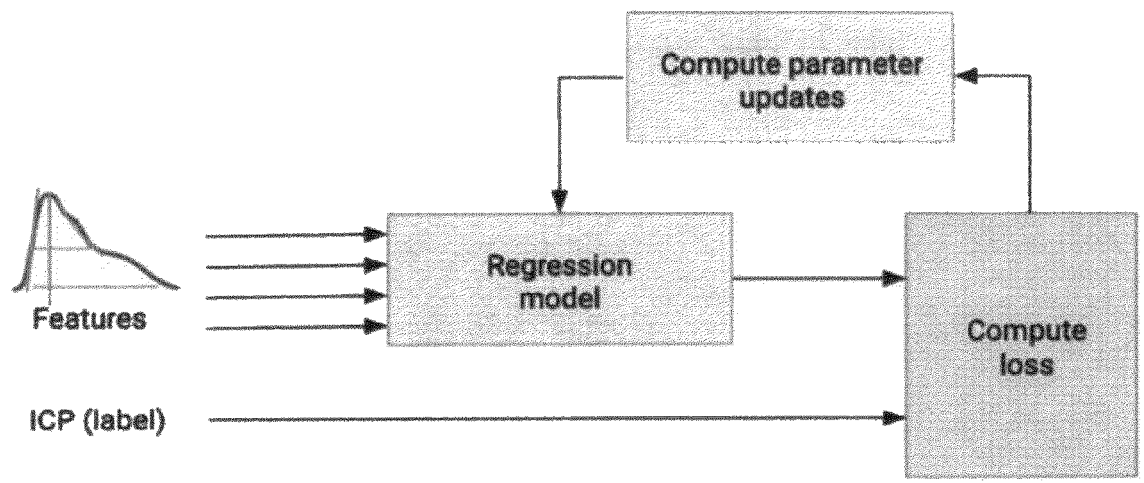
FIG. 7 is a diagrammatic representation of a multi-variable regression model.

In another envisaged arrangement depicted schematically in FIG. 7, an algorithm based on, for instance, multiple variable regression may be employed. Features from the acquired waveforms (such as one or more of the aforementioned features) are input into a model (prediction function) trained on data obtained in a clinical trial and labelled with target ICP values obtained using a gold standard method (such as an invasive ICP monitor). The weights of the inputs of the model are adjusted during training to produce the lowest error (cost function) between the predicted and target ICP values.

Figure 8:
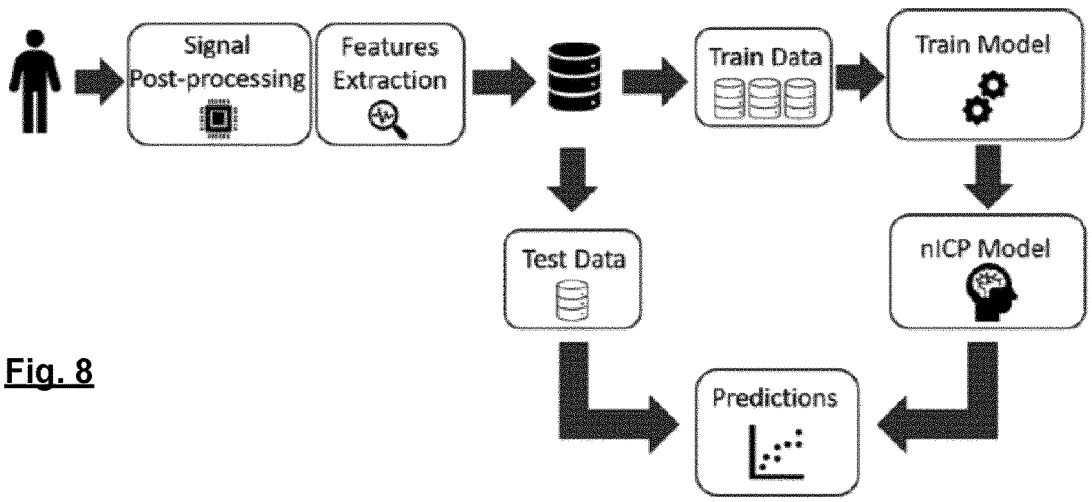
FIG. 8 is a diagrammatic representation of a process for generating the prediction model of FIG. 7.

FIG. 8 is a schematic representation of an illustrative process for establishing the aforementioned model.

Once the multi-wavelength optical signals are acquired from the patient's head, they undergo a post-processing stage. At this stage, the optical signals are filtered to remove noise and baseline drifts by means of digital signal processing filtering techniques. After filtering out noise, the pulsatile signals are then normalised by their DC baseline values (also filtered from the raw optical signals by low-pass filters). This normalisation process enables the ability to take into account of the proportion of total light absorbed, which may differ within patients, wavelengths or within measurements.

After signal filtering and normalisation, one or more of the features described above are extracted from the signal. The feature extraction can be performed in a rolling window with no prefixed length. As changes in the intracranial pressure (absolute) values are monitored for rather longer period, this rolling window's length can be from few seconds up to 2 minutes. Once the features are extracted within the rolling window, considering that a rolling window will contain more than one pulse, the features extracted for each pulse can be averaged across the number of pulses (i.e. one feature value for each rolling window).

After feature extraction and averaging within each rolling window, the extracted feature(s) are passed to a post-processing stage. In this stage, the features extracted are standardised to transform them into a gaussian (normal) distribution and to take into account of magnitude/scale differences between features. After standardisation, the n number of features extracted go a transformation process to maximise the variance captured.

The resultant data are then split into training and test data (at a discretionary ratio), following common Machine Learning techniques. The training data (usually 70-80% of total data) are used to train the prediction model, whereas the remaining data is held to later validate the performance of the model.

The model is then trained/built using supervised Machine Learning, where the target (known) intracranial pressure is used to construct a model that will predict the response variable (ICP) based on the input predictors (features). The prediction model will try to fit the response variable and predictors whilst minimising the error of prediction. In one illustrative implementation, the model is based on Support Vector Machines algorithms. However, another model among the many available, for instance Neural Network, could also be utilised.

After the model has been trained, it is then validated using the 'unseen' test data to verify the accuracy of prediction and, if required, optimise or change the model. Other validation techniques such as k-fold crossvalidation or Leave One Out Crossvalidation (LOOCV) can be used to validate the model.

Figure 9:
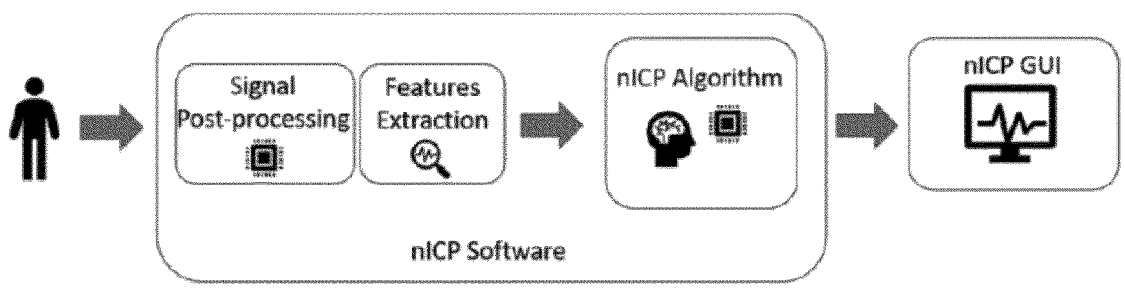
FIG. 9 is a diagrammatic representation of a process for generating real-time intracranial pressure predictions.

Once the prediction model has been finalised and validated, it can be implemented into a 'live' process implementing an algorithm/software that predicts intracranial pressure measurements in real-time, as shown in FIG. 9.

Different optical signals can be used to predict the intracranial pressure. The optical probe enables the collection of light at multiple (in this instance, four) different wavelengths, hence different options are available for this purpose. One illustrative option is to use a single wavelength at the isobestic point to extract the relevant features for intracranial pressure prediction. The advantage of using the isobestic wavelength is its independence from blood oxygenation. Another option is to obtain a pulsatile signal from the pulsatile component of the oxygenated haemoglobin (HbO2). By using two of the wavelengths, the oxygenated and deoxygenated haemoglobin signals can be spectroscopically separated. From this, the HbO2 can be used to extract the relevant intracranial pressure features.

Figure 10:
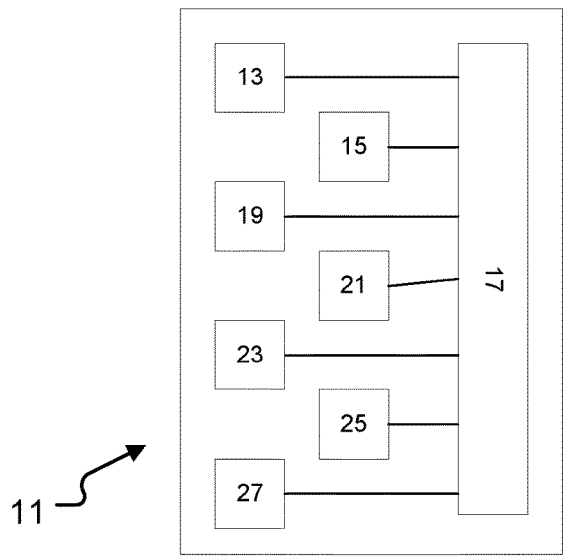
FIG. 10 is a schematic representation of an illustrative controller for use with the system disclosed.

FIG. 10 is a schematic representation of an illustrative controller 11 for use with aspects of the system disclosed. As aforementioned, the controller may advantageously comprise a laptop computer or other portable computing device.

The controller 11 comprises a power supply unit 13 that is configured to draw power from a mains power supply and regulate the supply of power to the remaining components of the controller. The controller 11 includes a processor 15 that is coupled to a system bus 17 by means of which signals can be sent between the processor and the other components of the controller. The controller 11 further comprises read only memory (ROM) and/or random access memory (RAM) 19 that provides a processing environment in which the processor 15 can execute computer programs. The controller also includes a data store 21 for the storage of computer programs for execution by the processor.

In this illustrative embodiment, the system bus 17 is coupled to a communications interface 23 (for example, an Ethernet and/or wireless interface), a peripheral interface 25 and a video controller 27. The peripheral interface 25 is configured to enable user interface devices, such as a keyboard and/or pointing device (such as a mouse or trackball), and ancillary equipment such as one or more printers to be connected to the hub for use therewith. The peripheral interface could include RS232 connectors, USB connectors, PS2 connectors or any other type of connector. The video controller 27 provides an interface that enables a display, not shown, to be coupled to the hub, and functions in response to signals from the processor to generate images for display on the display.

In the preferred arrangement, much of the functionality herein described is implemented in software, but it will be appreciated by persons skilled in the art that some or all of this functionality could alternatively be implemented in hardware (for example by means of one or more application specific integrated circuits (ASICs)) or by means of a combination of hardware and software. As such, the scope of the present invention should not be interpreted as being limited only to being implemented in software.

Figure 11:
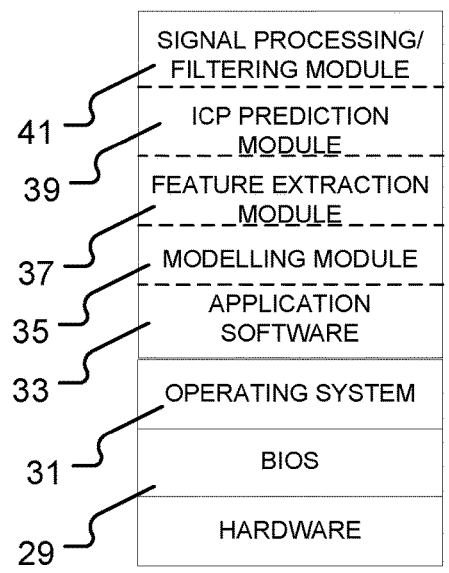
FIG. 11 is a schematic representation of illustrative software modules for implementing some or all of the functionality disclosed herein.

Referring now to FIG. 11, in the preferred arrangement the processor 15 and memory 19 cooperate to establish a BIOS (Basic Input/Output System) 29 that functions as an interface between the functional hardware components 31 of the controller and the software executed by the controller. The processor then loads from memory 19 an operating system 31 which provides an environment in which application software 33 (implementing some or all of the abovedescribed functionality) can run. In accordance with the preferred embodiment of the present invention, part of this functionality is provided by a modelling module 35, a feature extraction module 37, an intracranial pressure prediction module 39, and a signal processing/filtering module 41, the functions of each of which have been outlined above.

The reported nICP provides invaluable screening at the triage stage, indicating intracranial hypertension requiring imaging or intervention (such as CSF drainage). It also provides effective guidance for head injury management, notably ICP-targeted treatment regimes. Ultimately this could lead to significant improvements in secondary injury-related mortality, length of hospital stay and reduced post-trauma disability. It also finds application in causes of non-trauma related intracranial hypertension including meningitis, hepatic encephalopathy, hydrocephalus and severe migraine.

As aforementioned, aside from trauma, management of other conditions associated with intracranial hypertension (such as hydrocephalus, severe migraine and meningitis) could benefit from nICP monitoring. In many cases, especially borderline cases or those in early stages, the risk of invasive ICP monitoring is not justifiable; nevertheless intracranial monitoring could provide invaluable clinical information. The aforementioned non-invasive ICP monitor would also be an invaluable research tool both for investigation of pathophysiology and for assessment of the effectiveness of treatments for intracranial hypertension.

In addition to the foregoing, the teachings disclosed herein may be employed to infer a number of additional physiological parameters, such as:

Changes in cerebral blood volume (LICBV)—inferred from the change in total backscattered intensity.

Heart rate—obtained from the inter-beat intervals averaged over the sampling window.

Respiration rate—inferred by the frequency of periodic modulation of the pulse waveform.

Haemoglobin concentrations estimated spectroscopically from the simultaneous multi-wavelength measurements.

Oxy- and deoxygenated haemoglobin pulsations. As above, the raw multi-wavelength signals can be used to separate spectroscopically the 'pure arterial' and 'pure venous' pulsations.

Low frequency oscillations can be extracted from the signals. These can be used to estimate reactivity indexes (against systemic arterial blood pressure) for assessing the state of cerebral autoregulation (correlated with ICP).

It will be appreciated that whilst various aspects and embodiments of the present disclosure have heretofore been described, the scope of the present invention is not limited to the particular arrangements set out herein and instead extends to encompass all arrangements, and modifications and alterations thereto, which fall within the spirit and scope of the invention.

In particular, whilst particular combinations of features have been described herein, the scope of the present invention is not limited to the particular combinations set out herein, but instead extends to encompass any combination of features herein disclosed.

In addition, whilst certain arrangements have been described above in the context of software modules that are executable by a processor, it should be noted that the scope of the present invention is not limited to an implementation of the disclosure in software. Rather, the skilled person will immediately appreciate that the functionality described herein may equally be implemented in hardware (for example, by means of a plurality of application specific integrated circuits (ASICS)) or, indeed, by a mix of hardware and software.

Finally, it should be noted that any element in a claim that does not explicitly state "means for" performing a specified function, or "steps for" performing a specific function, is not to be interpreted as a "means" or "step" clause as specified in 35 U.S.C. Sec. 112, par. 6. In particular, the use of "step of" in the claims appended hereto is not intended to invoke the provisions of 35 U.S.C. Sec. 112, par. 6.

The invention claimed is:

1. A system for non-invasive in-vivo monitoring of intracranial pressure, the system comprising:

a probe comprising a plurality of optical emitters and a plurality of optical detectors, said optical detectors being configured to detect light emitted by said optical emitters and to generate signals representative of said detected light; and a controller comprising memory and a processor, the controller being connectable to the probe for energizing said optical emitters and receiving the signals from said optical detectors, wherein when said probe is attached to a head of a subject said signals are representative of light from said plurality of emitters that has been modulated by pulsation of cerebral arteries of said subject;

the system further comprising a modelling module, said modeling module comprising software code loadable into said memory for execution by said processor to establish a model relating morphological features of an optical signal to intracranial pressure, the optical signal being representative of a degree to which light input into a reference skull of a reference subject is absorbed by a reference brain of said reference subject, wherein said model comprises a prediction function trained on clinical trial data labelled with target intracranial pressure values, input weights for said model being adjusted during training to reduce error between predicted and target intracranial pressure values;

a feature extraction module comprising software code loadable into said memory for execution by said processor to extract one or more signal features from an absorbance signal derived from the signals generated by said detectors, said one or more signal features pertaining to morphological features of said absorbance signal; and an intracranial pressure prediction module comprising software code loadable into said memory for execution by said processor to input said signal features into said model and output an indication of intracranial pressure in accordance with said model.

2. A system according to claim 1, wherein said optical emitters are configured to be capable of emitting infra-red light.

3. A system according to claim 1, wherein said optical emitters are configured to emit light at a plurality of different wavelengths.

4. A system according to claim 1, wherein said optical emitters are configured to emit light at a wavelength selected from one or more of 810 nm, 770 nm, 855 nm, 880 nm, 780 nm, 805 nm, 850 nm, or 870 nm.

5. A system according to claim 4, wherein the plurality of optical emitters of said probe comprises four optical emitters, a first of said four emitters being configured to emit light having a wavelength of approximately 810 nm, a second of said four emitters being configured to emit light having a wavelength of approximately 770 nm, a third of said four emitters being configured to emit light having a wavelength of approximately 855 nm, and a fourth of said four emitters being configured to emit light having a wavelength of approximately 880 nm.

6. A system according to claim 1, wherein the plurality of optical detectors of said probe comprises only first and second optical detectors.

7. A system according to claim 6, wherein said first optical detector is closer to said plurality of optical emitters than said second optical detector so that a path length between said plurality of optical emitters and said first optical detector is smaller than a path length between said plurality of optical emitters and said second optical detector.

8. A system according to claim 1, wherein said one or more signal features extracted by said feature extraction module from said absorbance signal comprise one or more of: pulse amplitude, upstroke gradient, rise time, early diastolic decay rate, pulse width, late diastolic area under a curve, and total backscattered light.

9. A system according to claim 1, further comprising a signal processing/filtering module configured for processing and/or filtering the signals generated by said optical detectors.

10. A method of non-invasively predicting intracranial pressure in-vivo, the method comprising the steps of:

attaching a probe to outside of a head of a subject, the probe comprising a plurality of optical emitters and a plurality of optical detectors, the plurality of optical detectors being configured to detect light emitted by the plurality of optical emitters and to generate signals representative of said detected light, wherein said signals are representative of light from said plurality of optical emitters that has been modulated by pulsation of cerebral arteries of said subject;

loading modelling module software code of a modelling software module into memory and operating a processor to execute said modelling module software code to establish a model relating morphological features of an optical signal to intracranial pressure, the optical signal being representative of a degree to which light input into a reference skull of a reference subject is absorbed by a reference brain of said reference subject, said model comprising a prediction function trained on clinical trial data labelled with target intracranial pressure values, input weights of said model being adjusted during training to reduce error between predicted and target intracranial pressure values;

loading feature extraction software code of a feature extraction software module into said memory and operating said processor to execute said feature extraction software code to extract one or more signal features from an absorbance signal derived from the signals generated by the detectors of the probe provided on the subject's head, wherein said one or more signal features pertain to morphology of said absorbance signal; and loading intracranial pressure prediction software code of an intracranial pressure prediction software module into said memory and operating said processor to execute said intracranial pressure prediction software code to input said one or more signal features into said model to enable output of an indication of intracranial pressure in accordance with said model.

11. A system for non-invasive in-vivo monitoring of intracranial pressure, the system comprising:

probe means attachable to a head of a subject for purposes of monitoring intracranial pressure within said subject's head, said probe means comprising:

four optical emitter means, a first of said four optical emitter means being configured to emit light having a wavelength of approximately 810 nm, a second of said four optical emitter means being configured to emit light having a wavelength of approximately 770 nm, a third of said four optical emitter means being configured to emit light having a wavelength of approximately 855 nm, and a fourth of said four optical emitter means being configured to emit light having a wavelength of approximately 880 nm; and first and second optical detector means, said first optical detector means being is closer to said four optical emitter means than said second optical detector means so that a path length between said four optical emitter means and said first optical detector means is smaller than a path length between said four optical emitter means and said second optical detector means, said first and second optical detector means being configured to detect light emitted by said optical emitter means and to generate signals representative of said detected light;

said system further comprising:

control means comprising memory means and processor means, the control means being connectable to the probe means for energizing said four optical emitter means and receiving the signals from said first and second optical detector means, said signals being representative of light that has been modulated by pulsation of cerebral arteries of said subject;

wherein the memory means and processor means are co-operable to execute software code of a modelling software module, said modelling software module being operable to establish a model relating morphological features of a reference optical signal to intracranial pressure, the reference optical signal being representative of a degree to which light input into a reference skull of a reference subject is absorbed by a reference brain of said reference subject, wherein said model comprises a prediction function trained on clinical trial data labelled with target intracranial pressure values, input weights of said model being adjusted during training to reduce error between predicted and target intracranial pressure values;

said memory means and processor means are further co-operable to execute software code of a feature extraction software module that is operable to extract one or more signal features from an absorbance signal derived from the optical signals generated by said first and second optical detector means, said one or more signal features pertaining to morphology of said absorbance signal; and said memory means and processor means are further co-operable to execute software code of an intracranial pressure prediction software module that is configured to input said one or more signal features into the model established by said modelling software module and output an indication of intracranial pressure in accordance with said model.

* * * * *